US010478126B2

United States Patent
Najafi et al.

(10) Patent No.: US 10,478,126 B2
(45) Date of Patent: Nov. 19, 2019

(54) SMART CARPET SYSTEMS AND METHODS OF USING SAME FOR MONITORING PHYSICAL AND PHYSIOLOGICAL ACTIVITIES

(71) Applicant: Arizona Board of Regents on Behalf of the University of Arizona, Tucson, AZ (US)

(72) Inventors: Bijan Najafi, Houston, TX (US); Hyoki Lee, Tucson, AZ (US); He Zhou, Houston, TX (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/760,118

(22) PCT Filed: Sep. 15, 2016

(86) PCT No.: PCT/US2016/051969
§ 371 (c)(1),
(2) Date: Mar. 14, 2018

(87) PCT Pub. No.: WO2017/048977
PCT Pub. Date: Mar. 23, 2017

(65) Prior Publication Data
US 2018/0263565 A1    Sep. 20, 2018

Related U.S. Application Data

(60) Provisional application No. 62/218,919, filed on Sep. 15, 2015.

(51) Int. Cl.
*A61B 5/00*    (2006.01)
*A61B 5/024*    (2006.01)
(Continued)

(52) U.S. Cl.
CPC ............ *A61B 5/6892* (2013.01); *A61B 5/024* (2013.01); *A61B 5/0816* (2013.01);
(Continued)

(58) Field of Classification Search
CPC ...................................... A61B 5/6892
(Continued)

(56) References Cited

U.S. PATENT DOCUMENTS 8,186,231 B2    5/2012    Graumann et al.
8,904,876 B2    12/2014    Taylor et al.
(Continued)

FOREIGN PATENT DOCUMENTS

| DE | 102006061076 | 6/2008 |
|---|---|---|
| EP | 2336202 | 6/2011 |
| WO | WO 9426792 | 11/1994 |

OTHER PUBLICATIONS

International Search Report of PCT/EP2016/058156 dated Oct. 20, 2016, 4 pp.

*Primary Examiner* — Emily C Terrell
(74) *Attorney, Agent, or Firm* — Lathrop Gage LLP

(57) ABSTRACT

Systems and methods for using a smart carpet to monitor a health status of an individual. The smart carpet has electronics and a plurality of pressure sensing areas for sensing plantar pressure of the individual. A monitoring computer comprising a processor and a memory including machine readable instructions processes carpet data. A first part of the smart carpet is scanned at a first frequency and a second part of the smart carpet is scanned at a second frequency greater than the first frequency. Plantar pressures are received from the second part of the carpet and the instructions evaluate the plantar pressures to determine at least one of a physical
(Continued)

activity and a physiological activity. Where an emergency condition is determined, an alarm is communicated to monitoring personnel.

3 Claims, 11 Drawing Sheets

(51) Int. Cl.
    *A61B 5/08*     (2006.01)
    *A61B 5/103*     (2006.01)
    *A61B 5/11*     (2006.01)
    *A61B 5/113*     (2006.01)
    *G01L 1/22*     (2006.01)

(52) U.S. Cl.
    CPC ............ *A61B 5/1036* (2013.01); *A61B 5/112* (2013.01); *A61B 5/113* (2013.01); *A61B 5/1116* (2013.01); *A61B 5/1117* (2013.01); *A61B 5/1118* (2013.01); *A61B 5/1123* (2013.01); *G01L 1/225* (2013.01); *A61B 2562/046* (2013.01)

(58) Field of Classification Search
    USPC .................. 340/573.1, 572.1, 539.11–539.19
    See application file for complete search history.

(56) References Cited

U.S. PATENT DOCUMENTS

| | | | |
|---|---|---|---|
| 8,915,871 B2 | 12/2014 | Einav | |
| 2005/0046575 A1* | 3/2005 | Cooper | G08B 3/10 340/573.1 |
| 2007/0069021 A1* | 3/2007 | Elrod | G06K 17/00 235/451 |
| 2007/0159332 A1* | 7/2007 | Koblasz | G06F 19/3418 340/572.1 |
| 2009/0224925 A1* | 9/2009 | Gannot | A61B 5/1117 340/573.1 |
| 2010/0071482 A1* | 3/2010 | Graumann | G01L 1/205 73/862.381 |
| 2013/0066168 A1* | 3/2013 | Yang | A61B 5/0245 600/301 |
| 2015/0364023 A1* | 12/2015 | Hsu | G08B 21/043 340/573.7 |
| 2016/0217664 A1* | 7/2016 | Bradford | E04F 15/02 |

* cited by examiner ns and methods of using same for monitoring physical and physiological activities

RELATED APPLICATIONS

This application claims priority to U.S. Provisional Patent Application Ser. No. 62/218,919 titled "System And Methods For Automatically Recognizing And Tracking Physical And Physiological Activities For Healthcare Monitoring On A Smart Carpet", filed Sep. 15, 2015, the disclosure of which is incorporated by reference herein in its entirety.

FIELD OF THE INVENTION

This disclosure relates generally to monitoring body movement using a smart carpet. More specifically, the disclosure relates to monitoring systems and methods that employ a smart carpet to automatically track and evaluate health status and emergency conditions.

BACKGROUND

Falls and frailty are significant public health issues for successive aging in place. Current technologies are often impractical for tele-monitoring of falls, risk of falling, and frailty, where monitoring over months or years is required.

SUMMARY

Systems and methods for monitoring health status of one or more individuals using a smart carpet are disclosed herein. According to an embodiment, a method of using a smart carpet to monitor a health status of an individual is provided. The smart carpet comprises a plurality of pressure sensors arranged as a two-dimensional array. Each pressure sensor includes a block of anti-static foam situated between at least two perpendicularly oriented yarns. The method comprises operably coupling to the smart carpet a monitoring computer having a processor and non-transitory memory. The non-transitory memory has computer implemented instructions stored thereon. The method includes the step of simultaneously scanning a first part of the smart carpet at a first frequency and a second part of the smart carpet at a second frequency greater than the first frequency, and the step of receiving carpet data from the smart carpet over a communication pathway. The carpet data is processed using the computer implemented instructions to determine each of a physiological activity and a physical activity.

According to another embodiment, a smart carpet system for monitoring a health status of an individual includes a smart carpet having electronics and a plurality of pressure sensing areas for sensing plantar pressure. The system has a monitoring computer comprising a processor communicatively coupled to a memory. The memory includes machine readable instructions which, when executed by the processor, are capable of scanning a first part of the smart carpet at a first frequency and a second part of the smart carpet at a second frequency greater than the first frequency. Plantar pressures are received from the second part of the carpet and the instructions evaluate the plantar pressures to determine at least one of a physical activity and a physiological activity. Where an emergency condition is determined, an alarm is communicated to monitoring personnel.

According to yet another embodiment, a smart carpet system for monitoring a health status of an individual comprises a smart carpet having electronics and a plurality of pressure sensing areas for sensing plantar pressure of the individual. The system has an activity-determining processor configured to implement machine readable instructions to determine at least one of a physical activity and a physiological activity, and an interface configured to communicate results of the determination to remote monitoring personnel. The system includes an alarm generator configured to generate an alarm when the results indicate an emergency event.

DETAILED DESCRIPTION

Figure 1:
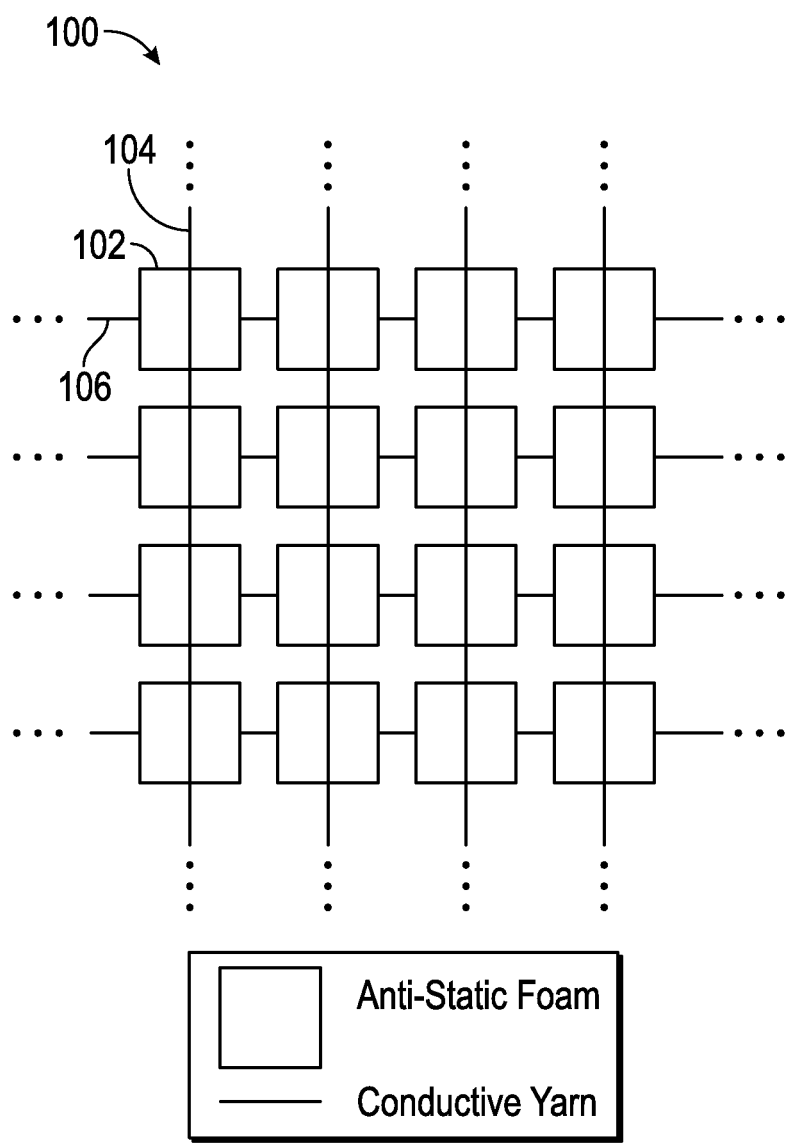
FIG. 1 schematically illustrates a portion of a smart carpet having a grid pressure sensor matrix made by conductive textile materials, in an embodiment.

Aging in place, i.e., the ability to continue to live safely in one's own home irrespective of age, is becoming more important due to the rapid increase in the population of senior citizens. The continued population growth of senior citizens may lead to significant financial and logistical burdens on the nation's healthcare system. As the population ages, there will be a greater need for preventive, acute, rehabilitative, and long-term health care services for senior citizens. Consistent healthcare monitoring, which is particularly essential for aging in place senior citizens, will also become increasingly important. An objective method for unobtrusive healthcare monitoring, useable by non-expert senior-citizens and in residential and community-care settings, is desirable. The present disclosure, among other things, relates to a context-aware smart carpet system for healthcare monitoring that is particularly useful for healthcare management of senior citizens.

A smart carpet system as a context-aware system for health status monitoring of senior citizens provides a practical form factor for remote and continuous screening of movements, and can be used to gather meaningful clinical information such as frailty, risk of falling, outcomes of rehabilitation, plantar wound dressing conditions, emergency conditions such as sudden falling due to heart attack, et cetera. Tomographic method-based and sensor array-based carpet systems in the prior art may allow for imaging and displaying position of footsteps. However, such systems are inadequate for health status monitoring as they neither provide meaningful clinical information nor recognize emergency conditions. Moreover, their exorbitant price prohibits installation in home environments. There is a need for unobtrusive health status monitoring systems and methods that operate unsupervised at any location (e.g. a person's home) to allow aging in place of senior citizens.

Indeed, aging in place is one of the key issues of modern societies. In 2029, more than 20% of the total US population will be over the age of 65, and by 2050, this population will have increased to 83.7 million people, almost double the 2012 population estimate of 43.1 million. Continued population growth of these older adults (age 65+) will lead to a greater need for preventive, acute, rehabilitative, and long-term health care services, as well as a need for tools to enable them to function independently during everyday activities.

Falls and frailty are significant public health issues for successful aging in place because they are the primary causes of injury and death in older adults. Falls are the second leading cause of accidental/unintentional deaths. Approximately 424,000 people die from falls each year and 37.3 million falls are severe enough to require medical attention. In 2013, the total direct medical cost of fall injuries for people over age 65 was $34 billion. And this cost associated with fall injuries is known to increase rapidly with age. Frailty is also a major health condition associated with aging and may increase the risk of falling, fear of falling, delirium, disability, hospitalization, long-term care, and even death. 25% to 50% of adults over age 85 are estimated to be frail. Frailty exacts a high cost on an individual in terms of quality of life, and the burden of frailty can affect the ability of older adults to live independently. Currently, physicians typically rely on basic physical examinations to assess frailty and risk of falling. As a result, only severe deficiencies are reliably identified. An objective method for assessing fall risk and frailty that can be employed by non-experts in a community-care setting would enable advanced screening for high risk individuals. However, there is currently no practical tool for everyday screening of fall risk and frailty during unsupervised conditions.

Remote monitoring systems have the potential to improve patient access to healthcare. Nearly 20% of people in the United States live in rural areas, but only 9% of physicians work in rural areas. Problems caused by lack of access to healthcare may exacerbate over time as many organizations predict there will be a shortfall in primary care providers due to recent health care reform. Rural residents have substantially poorer healthcare than urban residents. When compared to urban residents, rural residents travel 2 to 3 times farther to see a physician, see fewer specialists, and have worse health outcomes for common conditions such as diabetes and heart attack. Remote monitoring systems can extend the reach of physicians to underserved rural areas and consequently reduce these health disparities.

Tele-monitoring of falls, fall risk and frailty can support successful aging in place. Such monitoring may allow for evaluation of frailty progression and enables timely intervention after a fall, thereby promoting a more active lifestyle through a reduction in fear of falling. Monitoring daily activity patterns for fall risk and frailty would enable more accurate and up-to-date assessments of physical health as compared to infrequent physical exams. Such monitoring could also evaluate the efficacy of rehabilitation programs designed to reduce fall risk.

Tele-activity monitoring is commonly used to quantify daily activity. Most tele-activity monitoring devices are wearable motion monitoring devices such as a pedometer, actometer, accelerometer, and/or gyroscope attached to the patient's wrist, waist, or ankle. These devices have been widely used in clinical studies to monitor circadian rhythms, hyperactivity, diabetic care, sleep disorders and Parkinson's disease. Although some devices have been developed to monitor risk of falls and frailty, these devices have serious technological limitations such as short battery life, vision obstruction/occlusion problems with camera-based systems, and user resistance to wearing wearable sensors at all times.

A smart carpet as disclosed herein may be used for tele-activity monitoring and may track gradual changes in gait and motor performance. The smart carpet may also recognize emergency situations such as a falls or the inability to rise from the carpet. The carpet is a non-wearable system for tele-activity monitoring that may enable continuous, remote screening of fall risk and frailty based on a patient's motor performance and activities. If desirable, the carpet may also be combined with other means of measurement including wearable technology and camera based motion tracking systems.

The disclosed smart carpet may reduce fear of falling and promote active living in older adults, and as such, decrease the need for in-clinic monitoring. The smart carpet may be constructed from smart textiles, which have been successfully used for long-term monitoring of physiological parameters in a variety of healthcare domains such as tele-monitoring, rehabilitation, ergonomics, and sports medicine. Furthermore, smart textiles in the form of clothing and bedding have been used to monitor neurological and cardiovascular disorders and detect human motion. However, a smart textile-based carpet, practical for residential, nursing home, and acute settings, has not yet been developed to monitor, analyze, and assess fall risk and frailty.

The disclosed smart carpet may have a positive impact on the ability of older adults to age in place. The smart carpet may provide early detection of fall risk and frailty in older adults, which may result in fewer falls in this population. The smart carpet may be particularly beneficial in emergency situations (e.g., a fall during unaccompanied movement). Such reduction in the number of falls will help alleviate healthcare costs in older adults and improve quality of life by allowing senior citizens to remain in their homes. Continuous in-home tele-monitoring, as discussed herein, may also reduce the possibility of injury or death because it may request immediate assistance when a fall or other emergency condition is detected. The smart carpet may provide peace of mind to older adults fearful of injury and may enable them to feel comfortable aging in place, and consequently, improve their quality of life. The smart carpet may also monitor disease progression for diseases such as diabetes, stroke, and Parkinson's that affect mobility and balance. The smart carpet may conduct non-intrusive continuous daily activity monitoring of fall risk and frailty, and may advance the state of the art in fall risk assessment and continuous home-based health monitoring for successful aging in place.

The smart carpet may have several advantages over conventional physical activity trackers. One of the issues in fall risk assessment and activity tracking is the necessity of continual monitoring over extended periods of time (e.g., months or years). Many elderly people stop wearing sensors or carrying cellphones with monitoring applications over these long time periods. As such, a non-wearable monitoring device like the smart carpet has substantial advantages because it operates continuously without changing the user's normal routine and provides detailed data about gait and motor performance during locomotion, sitting, and standing. Research-grade smart rugs (e.g. GaitRite™ Walkway) that map the temporal pressure profiles of footsteps are used by research clinics, but they are not suitable for residential settings. For instance, they cannot be used on stairs due to their lack of flexibility, and their high cost renders them unsuitable for wall-to-wall arrangement in homes. And, to effectively detect emergency events and track deterioration in motor performance, such wall-to-wall and up-the-stairs monitoring in homes is a requirement.

The disclosed smart carpet uses highly flexible and washable conductive yarns as the sensing elements, which may be either attached to the underside of regular residential carpet or integrated directly into the carpet's fibers. Other flexible sensing units like hybrid flexible sensors may be also used to form the smart carpet. The smart carpet may be extremely flexible and may be easily folded and/or rolled up for storage or movement. The sensing elements may be washable, which may improve longevity. Moreover, the smart carpet may be economical because the conductive yarns and/or flexible sensing elements used in the carpet are inexpensive.

Prior art floor based sensing systems (e.g. SenFloor™) based on tomographic methods identify footstep and display position and footfall of a person walking on the floor. However, the use of fiber optics for sensing is often unsuitable for residential applications due to their high fragility and cost. Such systems also do not incorporate intelligent methods to extract clinically meaningful information related to risk of falling, frailty, and identification of emergency situations.

The disclosed smart carpet system may be used also to collect health status information, such as respiration rate, heart rate, and heart rate variability, by assessing fluctuation in plantar pressure of a person, as well as in-chair pressure during sedentary behavior. The smart carpet system may use this information to identify deterioration in health status or emergency events such as heart attack and/or stroke. The smart carpet system may also be used for tracking outcomes of an intervention, e.g., by monitoring changes in motor performance in Parkinson's as a function of medication or deep electrical stimulation, and may be used to track changes in pain status by determining the quality of motor performance, such as duration of rising from a chair, gait initiation, gait speed, et cetera.

The application of the disclosed smart carpet system is not limited to senior citizens or residential settings. By measuring heart rate, heart rate variability, respiration rate, et cetera, the smart carpet system may also unobtrusively track stress in office workers, and the information gleaned may be used for modifying environmental stressors to enhance well-being and health of office workers. The smart carpet system may also unobtrusively track mental stress including anxiety, depression, sleep disorders, etc., and may track unobtrusively cardiopulmonary activity related to sleep quality for monitoring and sleep disorders including sleep apnea, insomnia, and somnambulism.

The smart carpet system may also include other sensor modalities and/or may be combined with other types of sensors to track environmental information such as noise, humidity, air quality, light quality, physical activity, et cetera, to better track heath status and environmental factors which may impact health.

The smart carpet system may also track adherence to prescribed footwear by identifying and comparing foot print patterns to expected foot print patterns of the prescribed foot wear. This may have application for prevention of diabetic foot ulcers and/or management of wound healing in patients with diabetics.

The smart carpet system may also include an auditory sensor for identifying talking while walking and thereby operate to measure the ability of a person to walk while talking. The smart carpet may also assess motor performance while talking as compared to motor performance without talking, which information may be used to evaluate the cognitive status of the user.

Focus is directed now to FIG. 1, which schematically illustrates a portion of a smart carpet 100 having a grid pressure sensor matrix made by conductive textile materials. Each textile-based pressure sensor may be made with a square shaped section of anti-static foam 102 situated between two perpendicularly oriented conductive yarns 104, 106. The resistance value of each of the anti-static foam 102 and the conductive yarns 104, 106 may be inversely proportional to the pressure applied to the foam 102. When no pressure is applied to the anti-static foam 102, the resistance value of the foam 102 may be very high, and no current may be conducted therethrough. Electric current may flow through the foam 102 when pressure is applied to the foam 102.

The conductive yarns 104, 106 connecting each pressure sensor may be highly flexible. This characteristic may allow the smart carpet 100 to be easily spread out, packed up, and moved. Such flexibility may also allow the smart carpet 100 to be used in different residential settings (e.g., on stairs).

Figure 2:
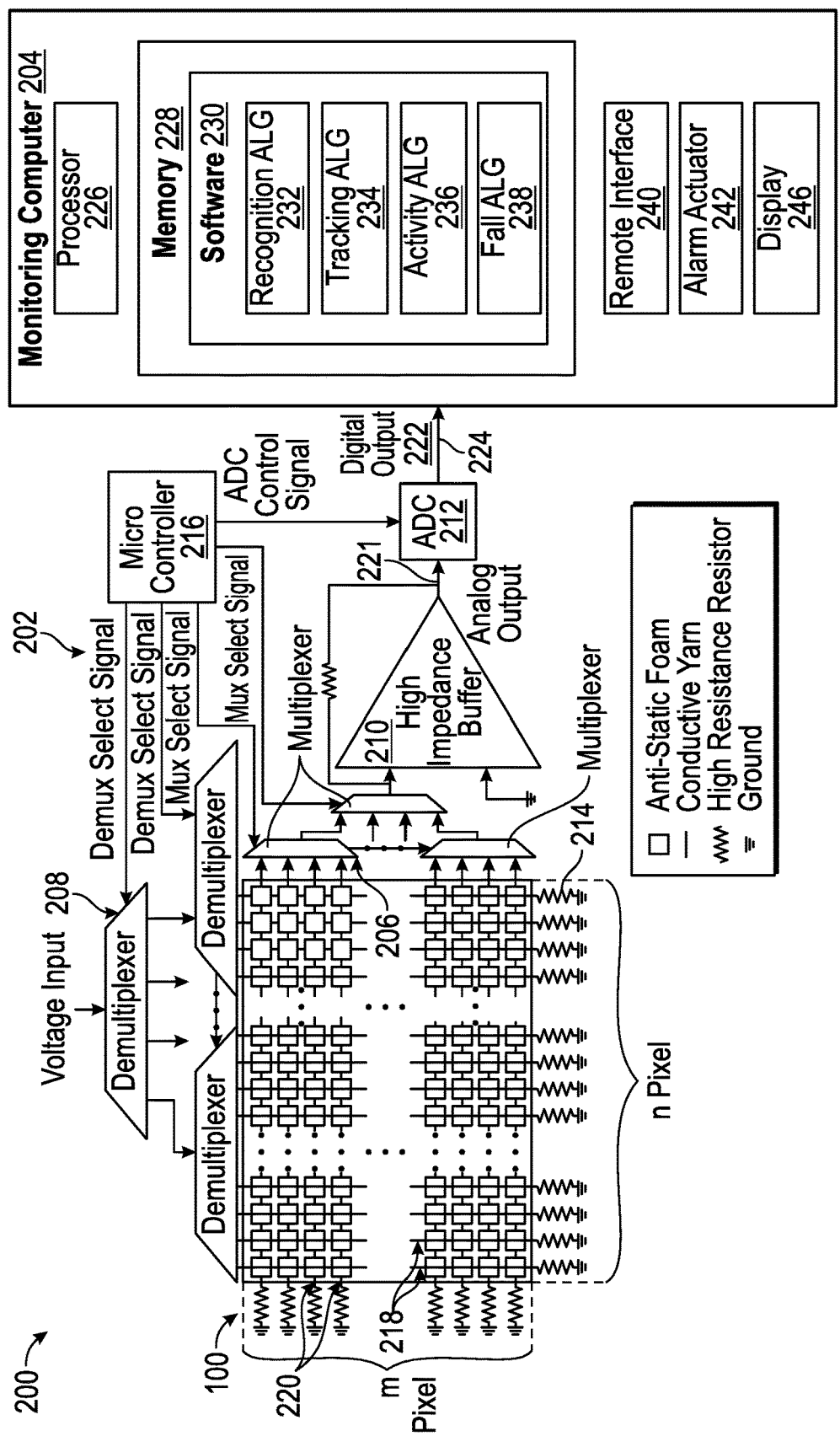
FIG. 2 shows one exemplary smart carpet system for automatically recognizing and tracking physical and physiological activities for healthcare monitoring, in an embodiment.

FIG. 2 schematically shows one exemplary smart carpet system 200 for automatically recognizing and tracking physical and physiological activities for health status monitoring. Smart carpet system 200 includes smart carpet 100 of FIG. 1 and associated circuitry 202 communicatively coupled to a monitoring computer 204.

Smart carpet 100 may consist of an m×n pressure sensor matrix with pixel resolution of 1 cm$^2$. The associated circuitry 202 may include one or more of: multiplexers 206, demultiplexers 208, high impedance buffer 210, analog-to-digital converter (ADC) 212, highly resistant resistors 214, and a microcontroller unit 216 (or another controller). In some example embodiments, the microcontroller unit 216 be configured through particularly configured hardware, such as an application specific integrated circuit (ASIC), field-programmable gate array (FPGA), et cetera, and/or through execution of software to perform functions in accordance with the disclosure herein.

Each pressure sensor may be located at the intersectional node of two perpendicular yarns (e.g., yarns 104, 106 in FIG. 1). DC voltage input may be applied on vertical yarns (referenced as yarns 218 in FIG. 2) and analog output voltage may be obtained on the horizontal yarns (referenced as yarns 220 in FIG. 2). To identify the pressed sensors, the whole grid matrix may be scanned one node by one node. At each instant, the DC input voltage may only be applied to one vertical yarn, and only one analog output may read from one horizontal yarn. If the corresponding sensor, which is located at the intersectional node of the two selected perpendicular yarns, is pressed, a non-zero analog voltage may be read at the output channel 221 as an input to the ADC 212. If the corresponding sensor is not pressed, the output reading may be zero.

The multiplexers 206, demultiplexers 208, and microcontroller unit 216 may be used to effectuate the sensor matrix scanning. Demultiplexers 208 may be used at input channels for the selection of vertical yarns 218, and multiplexers 206 may used at output channels for the selection of horizontal yarns 220. When the p-th horizontal yarn and the q-th vertical yarn are selected, the analog output may identify whether the (p, q)-th sensor is pressed or not.

The select signals of multiplexers 206 and demultiplexers 208 may be provided by the microcontroller unit 216. The microcontroller unit 216 may further be programmed to control the select signals in a desired frequency. At each clock cycle in the microcontroller unit 216, only one of the m horizontal yarns (i.e., yarns 220) and one of the n vertical yarns (i.e., yarns 218) are selected. If the sensor at the corresponding intersectional node is pressed, the resistance of the anti-static foam becomes low; electric current thus flows from the vertical yarn to the horizontal yarn, and a voltage output appears at the analog output channel 221. Since the resistance of the conductive yarns and the anti-static foam is pressure sensitive, the output voltage varies according to the applied pressure. After the analog-digital conversion at ADC 212, different analog voltages are transformed into corresponding digital levels indicative of the pressure at digital output 222, and the digital output 222 may be communicated to the monitoring computer 204. Smart carpet 100 measures relative pressure values (e.g., weight) of objects that are stationary or moving on its surface. System 200, via the monitoring computer 204, continuously monitors activity patterns of daily living and also automatically recognizes falling and other emergency situations to manage the healthcare of one or more people. System 200 may also be used to manage adherence to offloading in patients with diabetes, and other similar therapies.

The monitoring computer 204 may have at least one processor 226 and memory 228. The processor 226 represents one or more digital processors, and the memory 228 represents one or more of volatile memory (e.g., RAM) and non-volatile memory (e.g., ROM, Flash, magnetic media, optical media, et cetera). Software 230 may be stored in a non-transitory portion of the memory 228. The software 230 includes machine readable instructions that are executed by processor 226 to provide the functionality of the monitoring computer 204, as described herein.

In an example embodiment, software 230 includes a plurality of algorithms that operate to automatically recognize, track and detect activities such as one or more of daily living, a falling event, and frailty of individuals, to provide healthcare monitoring in places such as one or more of a residence, office, hospital, et cetera. For example, the software 230 may include a recognition algorithm 232, a tracking algorithm 234, an activity algorithm 236 for determining and monitoring activity, a fall algorithm 238 to determine a fall condition, et cetera. The processor 226 may receive digital data from the output 222 and process same to monitor the health of one or more individuals on the carpet 100. Monitoring computer 204 may also include a remote interface 240 for communicating with other computer devices, and an alarm actuator 242 for raising an alert when certain situations are detected on smart carpet 100. Monitoring computer 204 may in embodiments be combined with smart carpet 100 (e.g., at least some of the functionality thereof may be implemented using the microcontroller unit 216) without departing from the scope hereof.

The smart carpet digital output 222 may be communicated from the carpet 100 to the monitoring computer 204 over a pathway 224. The pathway 224 may be wired, wireless, or a combination of wired and wireless pathways. In an embodiment, a monitor (e.g., display 246 of monitoring computer 204) may be used to display the pressed sensor nodes. The digital output at the digital output 222 may be represented on the display 246 in such a way that the viewer can readily determine which nodes are being pressed and how much pressure is being applied each node relative to other nodes. For example, the monitoring computer 204 may be configured to present on the display 246 a color-coded map representing the pressure levels (e.g., the depressed foam squares may appear as red, blue, green, and yellow on the display 246 to indicate differing pressure levels). If the sensor at the corresponding intersectional node is not pressed, the resistance of the foam stays high, the foam is considered as "nonconductive" and both analog and digital outputs are zero.

System 200 is designed to be unobtrusive and nonintrusive when operating in any environment, and may include intelligent algorithms (e.g., algorithms 232, 234, 236, and 238) discussed in more detail below that cooperate to: (1) automatically distinguish between one or more individuals and objects by analyzing movements of these individual(s) and object(s) on the smart carpet 100; (2) classify activity patterns (e.g., classify that an individual on the smart carpet 100 is standing up from a sitting position, is sitting down from a standing position, is walking, is running, et cetera); (3) provide clinically meaningful information such as risk of frailty and risk of falling in elderly by quantifying key daily motor performances (e.g., number of times an individual sat during a predefined period, the speed at which the individual sat down, the quality of his turns, spatial temporal parameters of gait, gait initiation, gait variability, ability of walking while talking, et cetera, that are indicators of risk of falling and frailty status); (4) recognize effects of plantar wound dressing in patients with diabetes and their adherence to prescribed footwear; (5) automatically generate an emergency alarm signal to indicate an alarm condition (e.g., a falling event); and (6) provide output that may be combined with information from other fabrics, sensors (RF, Bluetooth, etc.), smart phones, and/or watches for data logging, transmitting and monitoring.

System 200 may operate in a real-time environment and under unsupervised conditions. Specifically, unlike other monitoring solutions that utilize sensors such as accelerometers, gyroscopes, and force sensitive resistors to identify movement of individuals, electrodes to acquire an electrocardiogram for evaluation of heart rate variability, and so on, system 200 may not require any additional sensors to capture similar information.

Figure 3:
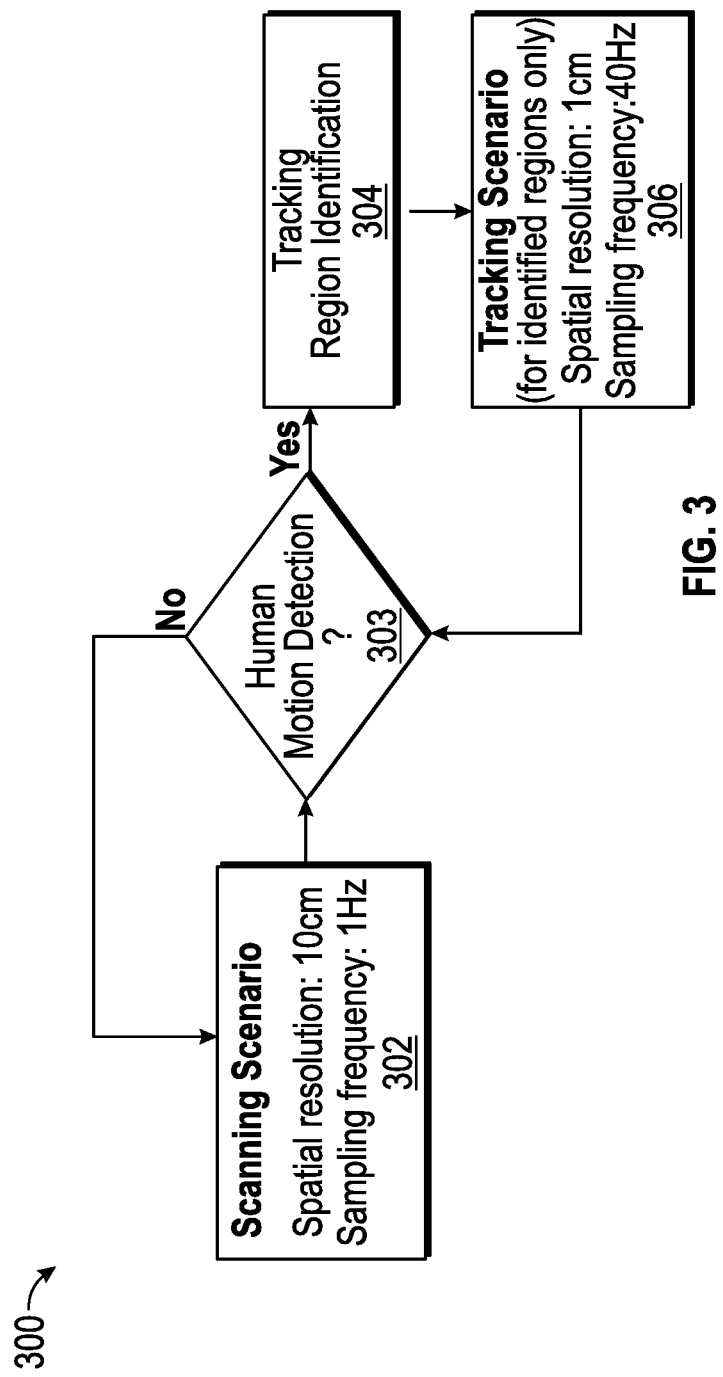
FIG. 3 is a flowchart illustrating an example high level algorithm for scanning and tracking movement on the smart carpet of FIG. 1.

FIG. 3 is a flowchart illustrating a high level algorithm 300 implemented by smart carpet system 200 of FIG. 2 for scanning and tracking movement on smart carpet 100 of FIG. 1 (using, e.g., the recognition algorithm 232 and the tracking algorithm 234). The algorithm 300 may have two high level scenarios: a scanning scenario 302 and a tracking scenario 306.

The system 200, via the monitoring computer 204, may employ scanning scenario 302 of the algorithm 300 to detect motion of one or more individuals. When in scanning scenario 302, smart carpet system 200 may operate with a low spatial resolution (for example 10 cm) and low sampling frequency (for example 1 Hz). In this example case, one in ten of the vertical yarns 218 and one in ten of the horizontal yarns 220 are scanned and the whole sensor matrix is scanned only once per second. Based on the result of the scan, the system 200 may detect human motion by using movement algorithms (described below). If no human motion is detected at step 303, smart carpet system 200 may continue to operate under only the scanning scenario 302 with low spatial resolution and low sampling frequency.

If human motion is detected on the smart carpet 100 at step 303, at step 304 the algorithm 300 may identify the location of the individual who is moving on the smart carpet 100 and demarcate a certain region (e.g., a 100 cm×100 cm region or another square region) with the human position as the midpoint. Then, tracking scenario 306 may be applied to the demarcated region(s) with high spatial resolution (for example 1 cm, so every vertical and horizontal yarn 218, 220 passing through the square region is scanned) and high sampling frequency (for example 40 Hz, so the whole sensor matrix in the square region is scanned forty times per second).

The high spatial resolution and high sampling frequency for the tracking scenario 306 may ensure accurate and meticulous human movement monitoring by system 200. The marked out square region location may be updated in real time with the human movement (i.e., the demarcated area being sampled at high frequency and high spatial resolution may be adaptively modified such that its midpoint generally corresponds to the current location of the individual). In an embodiment, while part of smart carpet system 200 is working under the tracking scenario 306, large areas of the carpet 100 may still be evaluated using the scanning scenario 302 because no motion has been detected in or immediately proximate these areas. The artisan will understand that the tracking scenario 306 may be more computationally intensive relative to the scanning scenario 302. By limiting the tracking scenario 306 to those regions of the carpet 100 on which movement is detected, costs associated with the system 200 may be reduced.

Figure 4:
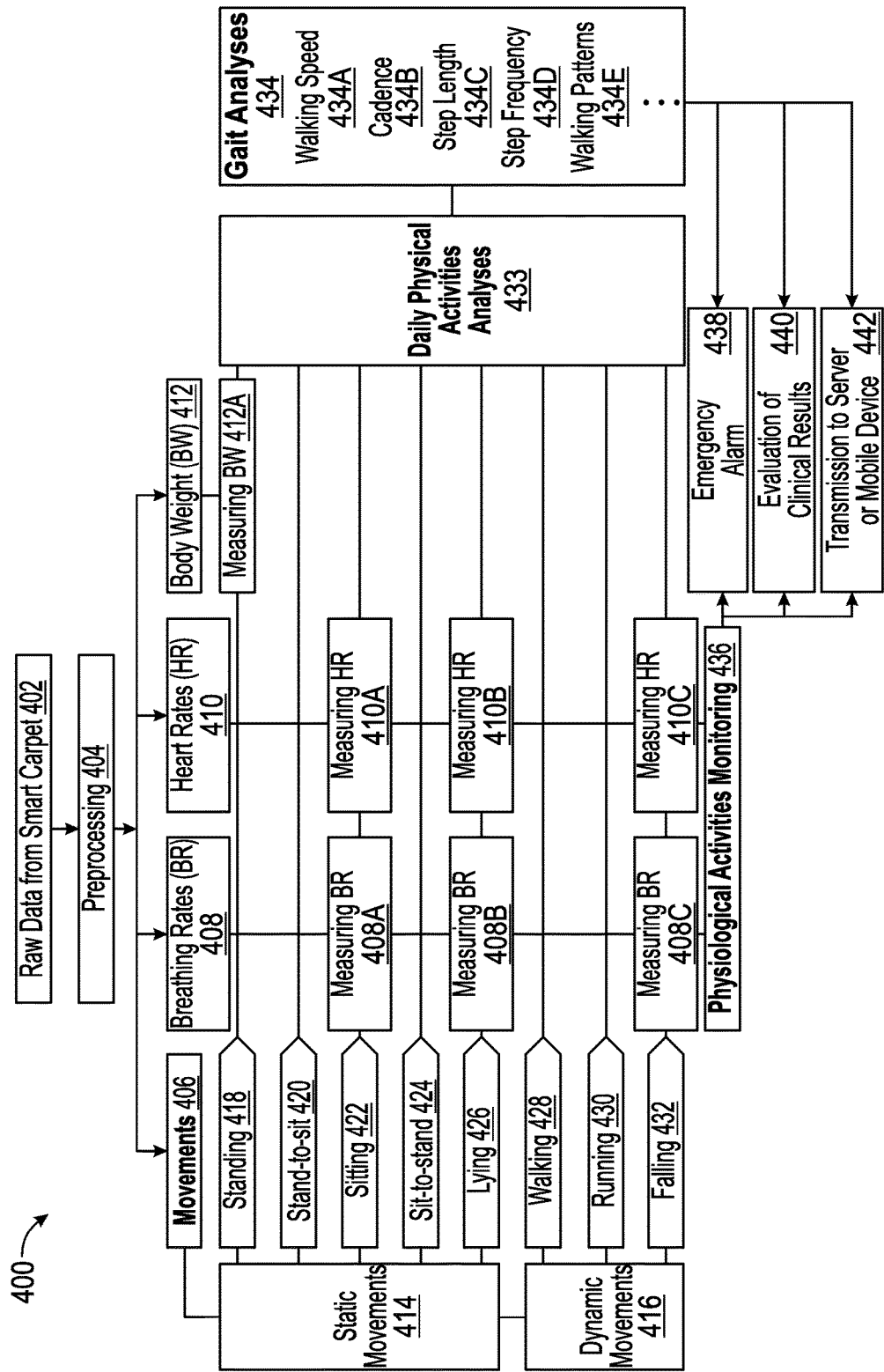
FIG. 4 is a flowchart illustrating an example high level algorithm, implemented using the system of FIG. 2, for recognizing and tracking the physical and physiological activities on the smart carpet of FIG. 1.

FIG. 4 is a flowchart illustrating a high level algorithm 400, implemented in system 200 of FIG. 2, for recognizing and tracking the physical and physiological activities on smart carpet 100 of FIG. 1. Algorithm 400 may be implemented at least in part within software 230 (e.g., some or more of the algorithm 400 may be implemented via the activity algorithm 236). Additional detail regarding the functionality of the algorithm 400 is provided in FIGS. 5-11 and the associated discussion below.

The algorithm 400 may begin at step 402, where the monitoring computer 204 may acquire raw data from textile-based sensors of the smart carpet 100 (e.g., via communication pathway 224 (FIG. 2)). As discussed in more detail herein, the amplitude of the raw data may depend on the weight of the human(s) or object(s) on the smart carpet 100.

The acquired raw data may then be preprocessed using signal processing techniques at step 404 so that high quality measurements (e.g., movement classifications, measurements of breathing rates, heart rates, body weight, et cetera) may subsequently be made. The preprocessing techniques at step 404 may include wavelet transform, filtering (e.g., digital low pass, high pass, or adaptive filtering), averaging, sampling, et cetera. The system 200 may use different optimal bandwidths for different purposes (e.g., different bandwidths may be used to classify movement, measurement of breathing rates, measurement of heart rates, measurement of body weight, et cetera).

Figure 5:
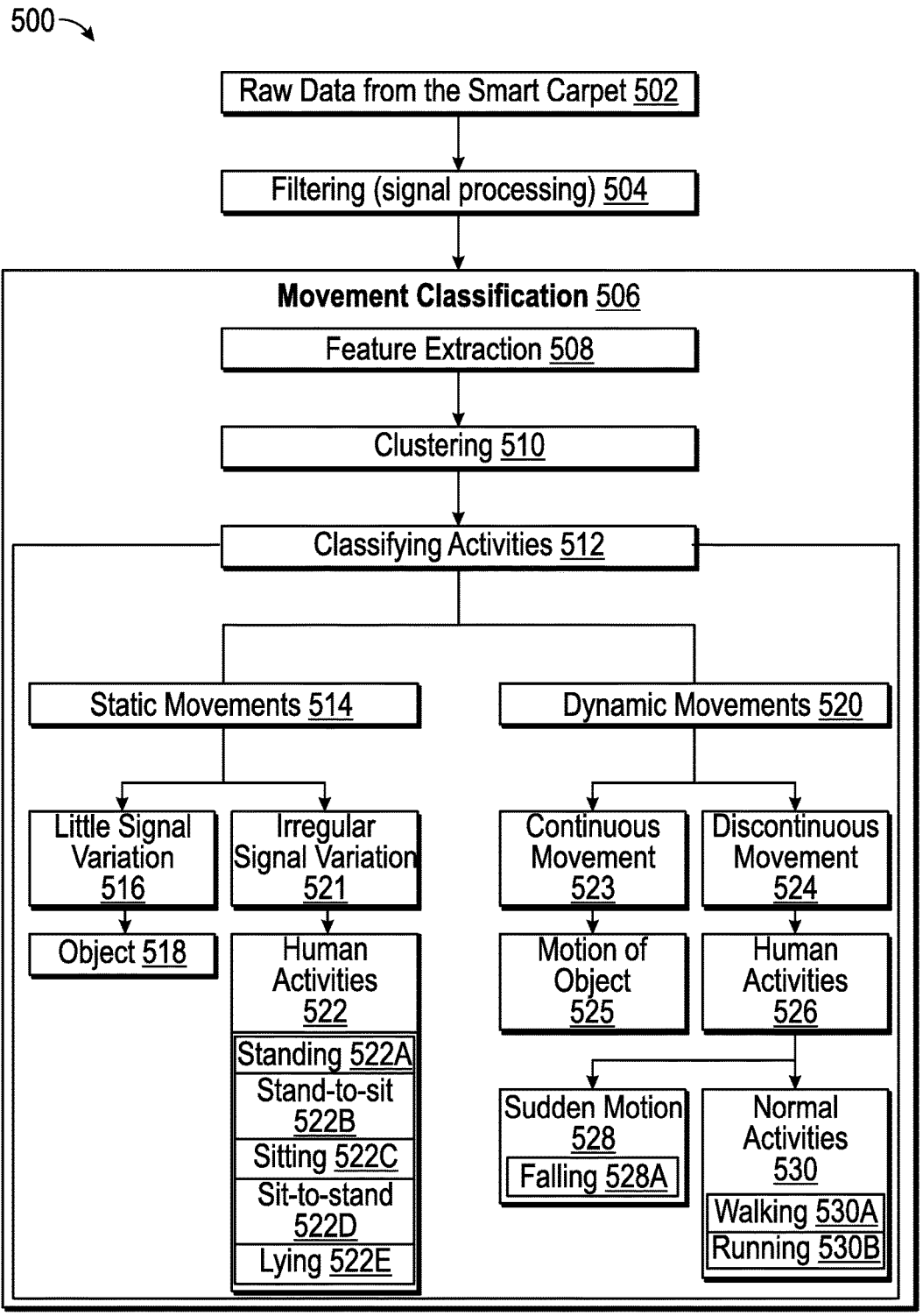
FIG. 5 is a flowchart illustrating further exemplary detail of the algorithm of FIG. 4 for identifying movements among one or more people as well as between people and objects, and for generating an emergency alarm when a person suddenly falls on the carpet of FIG. 1.

The preprocessed data may be used to determine movements at step 406. The movements of step 406 may be categorized in the system 200 as static movements 414 or dynamic movements 416. The static movement 414 categorizations may include standing 418, stand-to-sit 420, sitting 422, sit-to-stand 424, and lying 426; FIG. 10, discussed below, shows one example of how the different static movements 414 may be identified. The dynamic movement 416 categorizations may include walking 428, running 430, and falling 432. FIG. 5, discussed below, describes detailed methods for classification of various static movements 414 and dynamic movements 416.

The system 200, via the algorithm 400, may also calculate breathing rate 408 and heart rate 410, as discussed in more detail below with reference to FIG. 11. The system 200 may further be used to compute body weight 412 of a person on the carpet 100. As shown in FIG. 4, the breathing rate 408 may be measured at step 408A during sitting 422, at step 408B during lying 426, and during or immediately after a fall 432, using data acquired by the smart carpet 100. The breathing rate 408 may not be calculated for other movements (e.g., standing 418, stand-to-sit 420, et cetera). In an embodiment, the breathing rate 408 may be calculated while sitting 422, lying 426, and falling 432 over five seconds (or another unit of time) when the data indicates that the person on the carpet 100 is relatively stationary.

The heart rate 410 may likewise be computed during certain movements of step 406, but not at others. For example, as shown in FIG. 4, the heart rate 410 may be measured at steps 410A, 410B, and 410C only when the movements of step 406 are respectively categorized as sitting 422, lying 426, falling 432. Akin to the breathing rate 408, the heart rate 410 may be measured over five seconds (or another unit of time) when the data from the carpet 100 indicates that the person on the carpet 100 is relatively stationary. Body weight 412 may be measured only during standing 418 at step 412A.

Once the movements of step 406 have been categorized as static movements 414 or dynamic movements 416, the system 200 may use the various movement data to analyze the daily physical activities at step 433. At step 434, the system 200 may use the daily physical activity analysis performed at step 433 (or the movement data) to identify and evaluate spatial and temporal gait parameters 434. The spatial and temporal gait parameters 434 evaluated by the system 200 may include, for example, walking speed 434A, cadence 434B, step length 434C, step frequency 434D, walking pattern 434E, et cetera. The system 200 may also use the breathing rate 408 and heart rate 410 to monitor an individual's physiological activities at step 436.

The system 200 may be capable of generating an emergency alarm at step 438 in real-time if the temporal and spatial gait parameters 434 and/or the physiological activities monitoring 436 indicates an emergency or abnormal condition. For example, an alarm may be generated (e.g., a siren may go off) if the data indicates that the individual being monitored has fallen. The alarm 438 may also be communicated to remote monitoring personnel in one or more ways (e.g., the system 200 may cause a phone call to be placed to paramedics and/or may page a physician). In some embodiments, to reduce the risk of false alarms, the alarm 438 may be generated when at least two conditions are met. For example, the alarm 438 may be generated when the individual being monitored falls and stays down (e.g., lying 426) for ten seconds (or another unit of time); or, for example, the alarm 438 may be generated where the heart rate of the monitored individual appears abnormal in two (or more) successive readings.

At step 440, the clinical results may be evaluated. Specifically, the spatial and temporal gait parameters 434 and the physiological activities monitoring 436 results may be evaluated to determine clinical results (e.g. risk of frailty, effect of plantar wound dressing, et cetera).

The results (and/or the raw data) may be communicated by the system 200 to a server or mobile device at step 442 (e.g., the server associated with a senior care facility or hospital and/or the mobile device of a family member). This transmission may be in real-time, or data may be stored and transmitted on a period basis (e.g., once every day).

FIG. 5 is a flowchart illustrating algorithm 500 for categorizing movement of individuals as discussed above with respect to FIG. 4. The algorithm 500 may be used to classify the movement of an individual, to distinguish between the movement of two or more individuals or objects, and to generate an alarm as discussed above for FIG. 4. The algorithm 500 may be implemented at least in part by processor 226 and software 230.

At step 502, the monitoring computer 204 (FIG. 2) may acquire raw data from the smart carpet 100. At step 504, the raw data may be preprocessed (e.g., filtered, averaged, sampled, et cetera) as discussed above for step 404 of algorithm 400. At step 506, movement may be detected and classified.

The movement classification step 506 may involve extraction of various features from the preprocessed data at step 508. The feature extraction step 508 may include signal processing techniques such as time-domain processing (mean, standard deviation, skewness, kurtosis, velocity, acceleration, jerk, etc.), frequency-domain processing (fast Fourier analysis, power spectrum analysis, etc.), time-frequency coefficient analysis, wavelet coefficients, etc. Among the recognized features, the optimized features may be clustered for selection.

The clustering step 510 may involve grouping of optimized and selected features. The clustering step 510 reveals whether the data in some positions is due to human movement or object movement. For example, where the data indicates that the area on the smart carpet 100 on which pressure is applied is in the shape of human feet, the system 200 may determine that the movement is that of an individual. Alternately, where the area on the smart carpet 100 on which pressure is applied is in the shape of an object (e.g., wheels of a wheelchair), the system 200 may determine that the detected movement is object movement. The clustering step 510 may further show the number of people on the carpet (e.g., if there are two separate areas on which pressure is applied and each of them is in the shape of human feet, the system 200 may recognize that two individuals are standing on the carpet 100).

Based on the clustering step 510, the various static and dynamic movements of humans and objects may be classified at step 512. The classification step 512 may involve implementation of pattern recognition techniques, such as artificial neural networks, support vector machines, Bayesian classification, hidden Markov model, etc. The remaining steps 514-530 of the algorithm 500 may be implemented as part of the activity classification step 512.

More specifically, the system 200, via the software 230, may identify static movements 514 where there is little signal variation or where the signal variation is irregular. Where little signal variation is determined at step 516, the system 200 may characterize the movement as that of an object at step 518, as people cannot stand without appreciable motion (because of heart activity, breathing, et cetera).

Where irregular signal variation is determined at step 521, the system 200 may classify the static movement as human activity at step 522. Static human activities may include standing 522A, stand-to-sit 522B, sitting 522C, sit-to-stand 522D, and lying 522E (i.e., activities performed while the monitored individual is generally confined to the same area of the carpet 100).

The static human activity 522 may be characterized as standing 522A where the clustered area resembles the shape of feet and the signal amplitude is relatively large (i.e., the plantar pressure being applied to the smart carpet 100 is relatively high because of the weight of the human). If the signal amplitude successively decreases from a standing condition, the system 200 may determine a stand-to-sit activity 522B, as also discussed with respect to FIG. 10 below. The system 200 may identify the human activity 522 as sitting 522C where the clustered area shape resembles that of the monitored individual's feet (or part thereof), and where the signal amplitude is relatively faint (i.e., the full weight of the human is not being carried by the feet). The system 200 may determine sit-to-stand activity 522D where from the sitting activity the signal amplitude successively increases (indicating that the weight of the human is being borne by the feet). Where the clustered area is large (e.g., over five feet long), the system 200 may determine a lying activity 522E. The system 200 may be programmed to have different thresholds to allow for monitoring individuals having differing weights and sizes.

The system 200 via the algorithm 500 may classify dynamic movement at step 520. Dynamic movement 520 may be identified if one or more objects or humans traverse an appreciable area (e.g., one foot, two feet, et cetera) within a given time period (e.g., within five seconds, within three second, and so on).

If the dynamic movement 520 is continuous movement as determined at step 523, the system 200 may classify the movement as the movement of an object at step 525. Movement of an object may be classified at step 525 as object movement where the clustered area moves continuously and smoothly on the carpet 100 (e.g., indicating the movement of the wheels of a wheelchair).

If, on the other hand, the dynamic movement 520 is discontinuous as identified at step 524, the system 200 may at step 526 categorize the dynamic movement as human activity. For example, if the clustered area changes appreciably with time (e.g., changes from big in a first area to small then to big again in a second area proximate the first area to represent the pressure applied by the feet while the individual is moving), the system at step 526 may categorize the dynamic activity as human activity.

Human activity 526 may further be categorized as one of sudden motion at step 528 or normal activities at step 530. Sudden motion 528 may be for example falling 528A or another sudden motion. The system 200 may identify falling at step 528A where the signal amplitude suddenly increases abnormally. In some embodiments, to identify falling, the system 200 may also determine whether the area on the carpet 100 on which pressure is applied is relatively large.

Where the variation of the signal amplitude is within a given threshold (i.e., is low), the system 200 may identify the normal activity 530 as walking at step 530A or running at step 530B. If the signal amplitude changes slowly, the system 200 may identify the normal activity 530 as walking at step 530A. Where the signal amplitude changes quickly, the system 200 may identify the normal activity 530 as running 530B. As before, in identifying these normal activities 530, the system 200 may also confirm that the area on the carpet 100 on which pressure is being applied indicates the presence of human feet.

Figure 6:
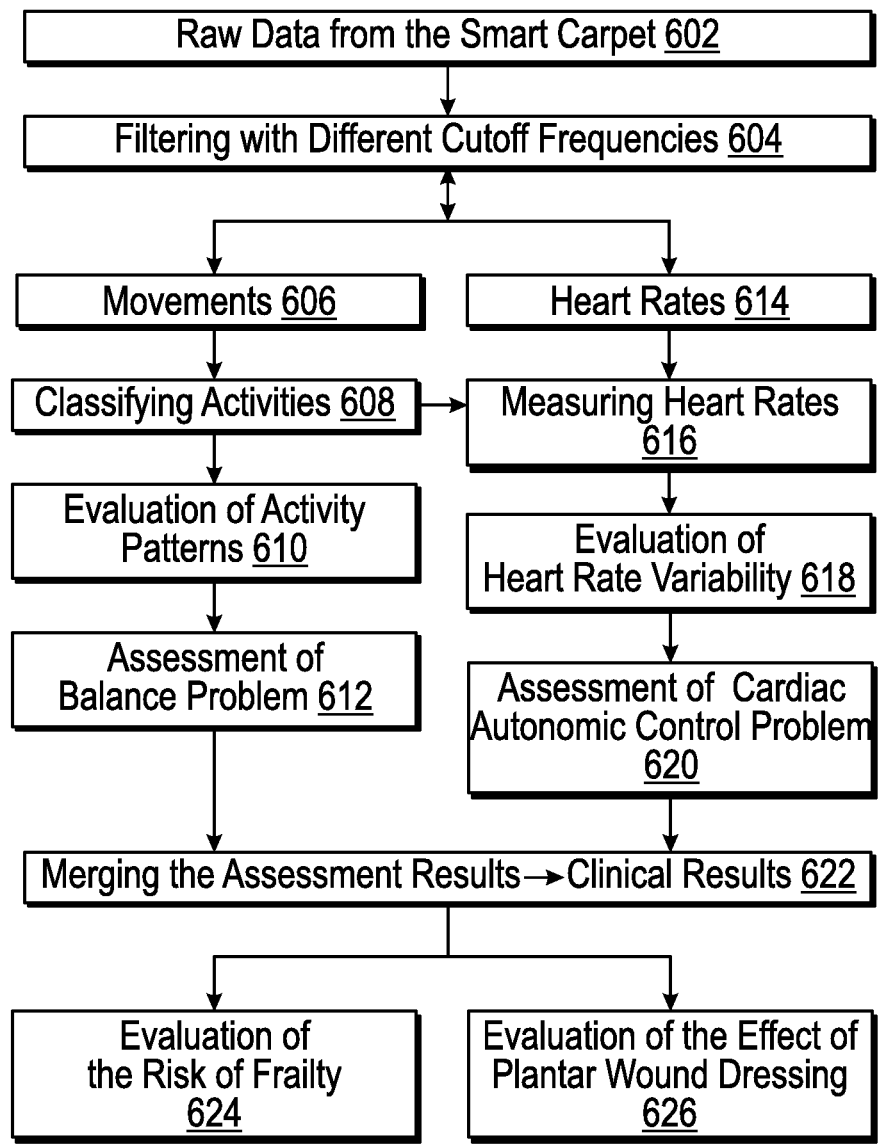
FIG. 6 is a flowchart illustrating further exemplary detail of the algorithm of FIG. 4 to evaluate clinical results for activity detected on the carpet of FIG. 1 using the system of FIG. 2, in an embodiment.

FIG. 6 is a flowchart illustrating algorithm 600, and provides further exemplary detail of algorithm 400 of FIG. 4 to evaluate clinical results for activity detected by carpet 100 of FIG. 1 using system 200 of FIG. 2. The clinical results include the risk of frailty in elderly and the effect of plantar wound dressing in patients with diabetic foot ulcers.

At step 602, the system 200 (e.g., monitoring computer 204), via the algorithm 600, may acquire raw data from textile-based sensors of the smart carpet 100 (e.g., over communication pathway 224). At step 604, the system 200 may adaptively filter the data using different cutoff frequencies to identify different movements, as discussed above for FIGS. 4 and 5. More specifically, the system 200 may determine movement at step 606, as set forth above for step 506 of the algorithm 500. At step 608, as discussed above for step 512 and associated steps of algorithm 500, the system 200 may classify the movement activity (e.g., as static movement and dynamic movement). At step 610, after the movement activities have been classified, the system 200 may evaluate activity patterns (e.g., determine that the monitored individual(s) are not lying down during the day for an extended period of time, have not fallen, et cetera). The criteria used for such evaluation may be different for different individuals (e.g., activity patterns may be evaluated differently for a mobile 60 year old individual and a relatively sedentary 95 year old individual).

At step 612, the system 200 may assess if the monitored individual has a balance problem. The system 200 may determine a balance problem at step 612 if it senses asymmetry in standing balance, abnormal waking speed, an irregular walking pattern, et cetera.

In addition to classifying movements, the system 200, via the algorithm 600, may monitor heart rates at step 614. Specifically, the system 200 may measure heart rates at step 616 after the movement activities have been classified at step 608. Such may allow the system 200 to take into account the movement activity in the heart rate measurements. For example, the system 200 may determine that a relatively high heart rate is not a cause for alarm where the monitored individual is walking or running, et cetera.

The system 200 may evaluate the variability of the heart rate at step 618. Testing for such heart rate variability may allow the system 200 to recognize, for example, cardiac autonomic control problems.

At step 622, the system 200 may merge the gleaned movement information with the physiological assessments to obtain clinically viable information about the monitored individual. For example, at step 624, the system 200 may use the clinical results to evaluate the risk of frailty of the monitored individual. Or, for example, at step 626, the system 200 may evaluate the effect on an individual of plantar wound dressing (e.g., compare actual foot print patterns to expected foot print patterns).

Figure 7:
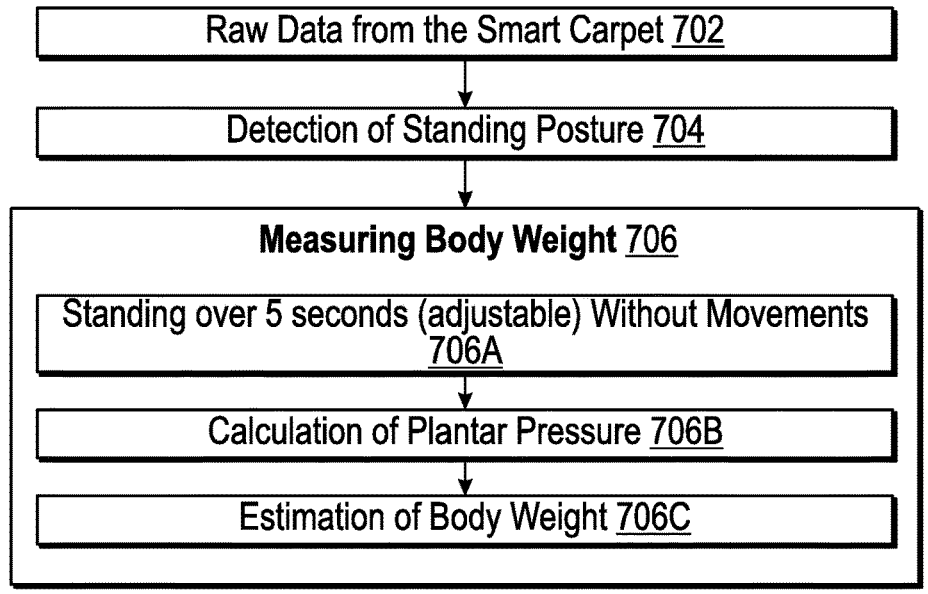
FIG. 7 is a flowchart illustrating further exemplary detail of the algorithm of FIG. 4 for measuring weight of a person on the carpet of FIG. 1 using the system of FIG. 2.

FIG. 7 is a flowchart illustrating a method 700, and provides further exemplary detail of algorithm 400 of FIG. 4 for measuring weight on carpet 100 of FIG. 1 using the system 200 of FIG. 2.

At step 702, the monitoring computer 204 may acquire raw data from textile-based sensors of the smart carpet 100 (e.g., via communication pathway 224). At step 704, the system 200 may ascertain that the monitored individual is standing. For example, the system 200 may determine that the monitored individual is standing where the clustered area resembles the shape of human feet and the signal amplitude is relatively large.

At step 706, the system 200 may measure the body weight of the monitored individual. Body weight measurement at step 706 may include sub-steps 706A, 706B, and 706C. At step 706a, the system 200 may wait until it determines that the monitored individual has been standing for over five seconds (e.g., that there has been no large movement on the carpet 100 for five seconds or another time unit) so as to obtain a reliable reading. At step 706B, the system 200 may calculate the plantar pressure being applied to the carpet 100 by the monitored individual (or group of individuals). At step 706C, the system 200 may estimate the body weight of the monitored individual(s) using the calculated plantar pressure. The artisan will understand that the plantar pressure may correlate to the body weight of the individual. In an embodiment, in estimating the body weight, the system 200 may also take into account the size of the area of the carpet 100 on which pressure is being applied.

Figure 8:
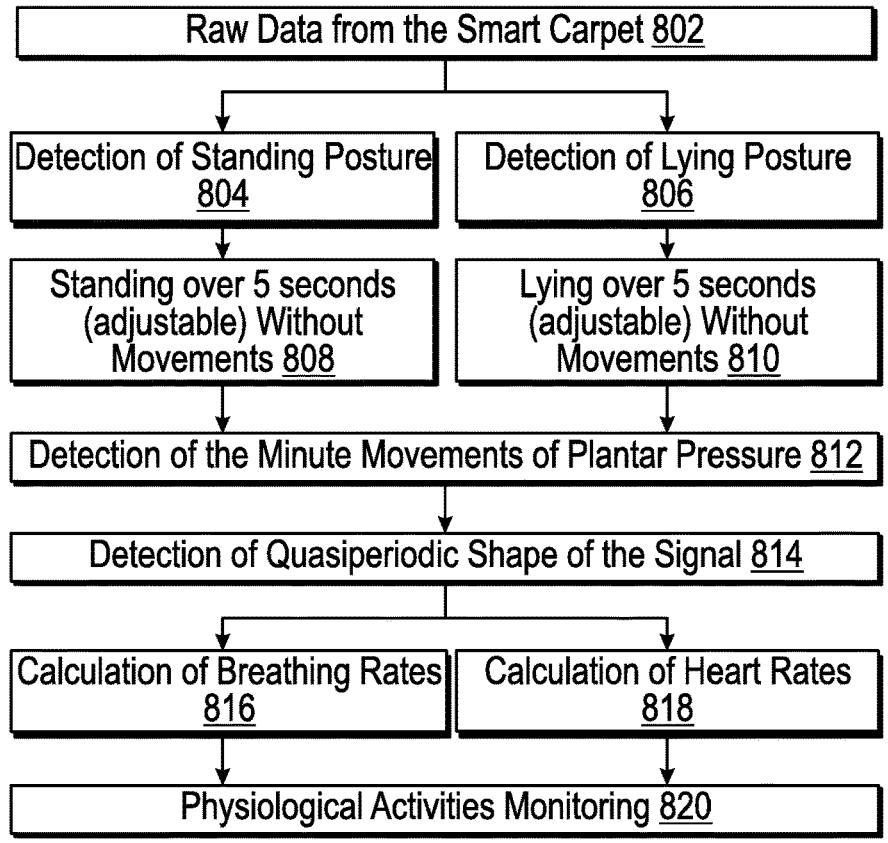
FIG. 8 is a flowchart illustrating further exemplary detail of the algorithm of FIG. 4 for calculating breathing and heart rates of a person on the carpet of FIG. 1 using the system of FIG. 2.

FIG. 8 is a flowchart illustrating a method 800, and provides further exemplary detail of algorithm 400 of FIG. 4 for calculating breathing and heart rates on carpet 100 of FIG. 1 using system 200 of FIG. 2.

At step 802, the monitoring computer 204 may acquire raw data from textile-based sensors of the smart carpet 100. At steps 804 and 806, the system 200 may determine whether the monitored individual is standing or lying, respectively. If the monitored individual has been standing for over five second (or a different time unit, e.g., ten seconds) without appreciable movement at step 808, at step 812, the system 200 may determine the minute (i.e., fine) movements of plantar pressure, as shown in the plantar pressure raw signal in FIG. 11 for example. Similarly, if the monitored individual has been lying for five seconds (or a different time unit) at step 810, the system 200 may determine the minute movements of plantar pressure at step 812.

Figure 11:
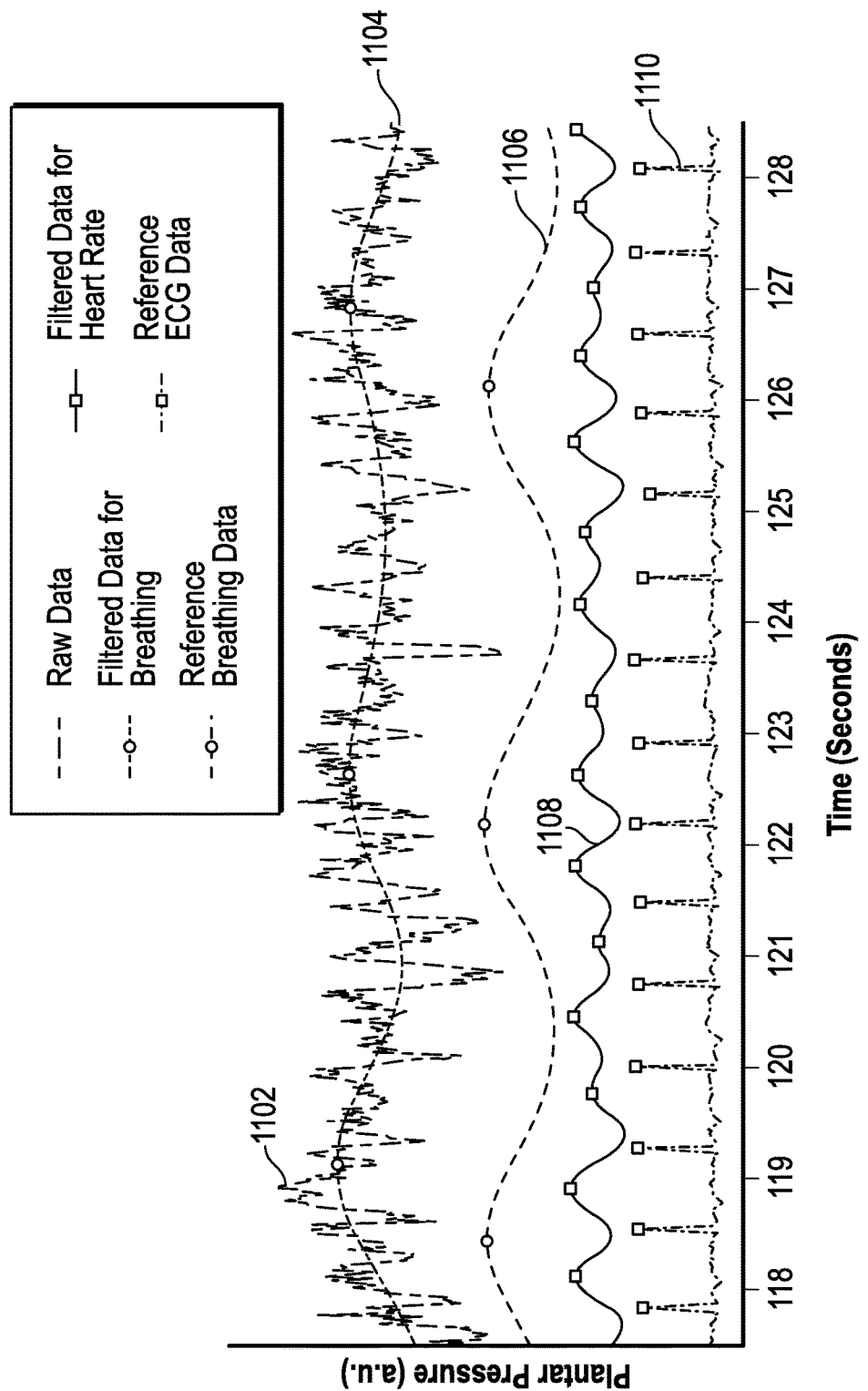
FIG. 11 shows exemplary signal processing by the system of FIG. 2 to determine breathing rate and heart rate from data of the smart carpet of FIG. 1, in an embodiment.

At step 814, the system 200 may detect the quasi-periodic shape of the filtered signal so as to extract breathing and heart rates at steps 816 and 818, respectively, as shown in more detail in FIG. 11. At step 820, the system 200 may use the determined breathing and heart rates to monitor physiological activities of the monitored individual or group of individuals. If an abnormal or emergency condition is detected, monitoring personnel may be apprised of same in real time (e.g., via remote interface 240 and/or alarm actuator 242).

Figure 9:
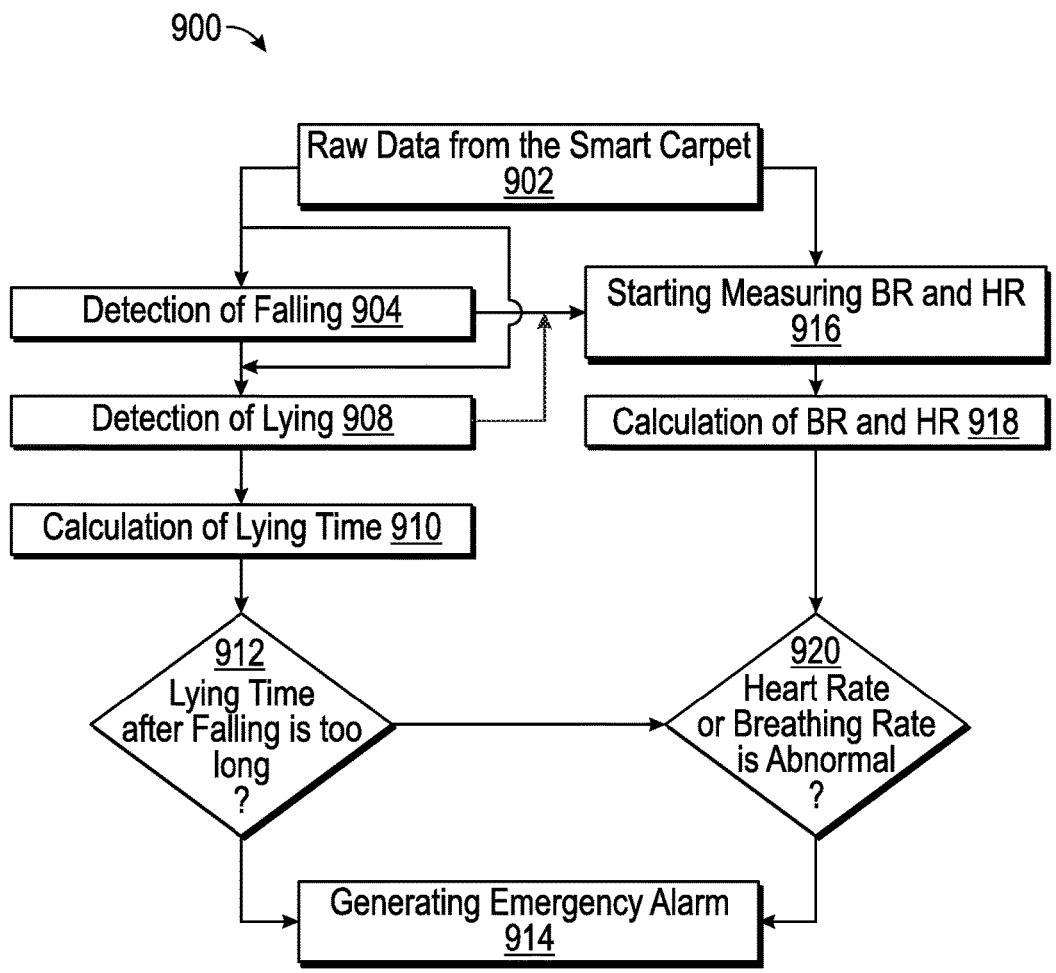
FIG. 9 is a flowchart illustrating further exemplary detail of the algorithm of FIG. 4 for generating an emergency alarm when a person suddenly falls on the carpet of FIG. 1.

FIG. 9 is a flowchart illustrating algorithm 900, and provides further exemplary detail of algorithm 400 of FIG. 4 for generating an emergency alarm when somebody has fallen suddenly on carpet 100 of FIG. 1 using system 200 of FIG. 2.

At step 902, the system 200 may, where applicable, detect falling as discussed above (e.g., for step 528A of algorithm 500). If the monitored individual is determined to have fallen, or where he is simply lying as detected at step 908, the system 200 may calculate the time of lying movement at step 910. At step 912, the system 200 may determine whether the lying time as detected at step 910 is abnormal (e.g., is too long, such as over ten seconds). If so, the system 200 may generate an emergency alarm at step 914 to apprise monitoring personnel (e.g., remote monitoring personnel) of the emergency condition.

The system 200 may also concurrently evaluate the physiological conditions of the monitored individual(s). Specifically, at step 916, after the detection of falling at step 904 and/or after the detecting of lying at step 908, the system 200 may measure the heart rate and breathing rates at steps 916 and 918. At step 920, the system 200 may determine whether the heart rate or the breathing rate is abnormal for lying posture. If so, the system 200 may generate the emergency alarm (e.g., as discussed above for step 438 of algorithm 400). In some embodiments, the system 200 may also take into account an abnormal lying and/or falling time (as determined at step 912) in determining whether the heart rate and/or breathing rate is not as expected.

Figure 10A:
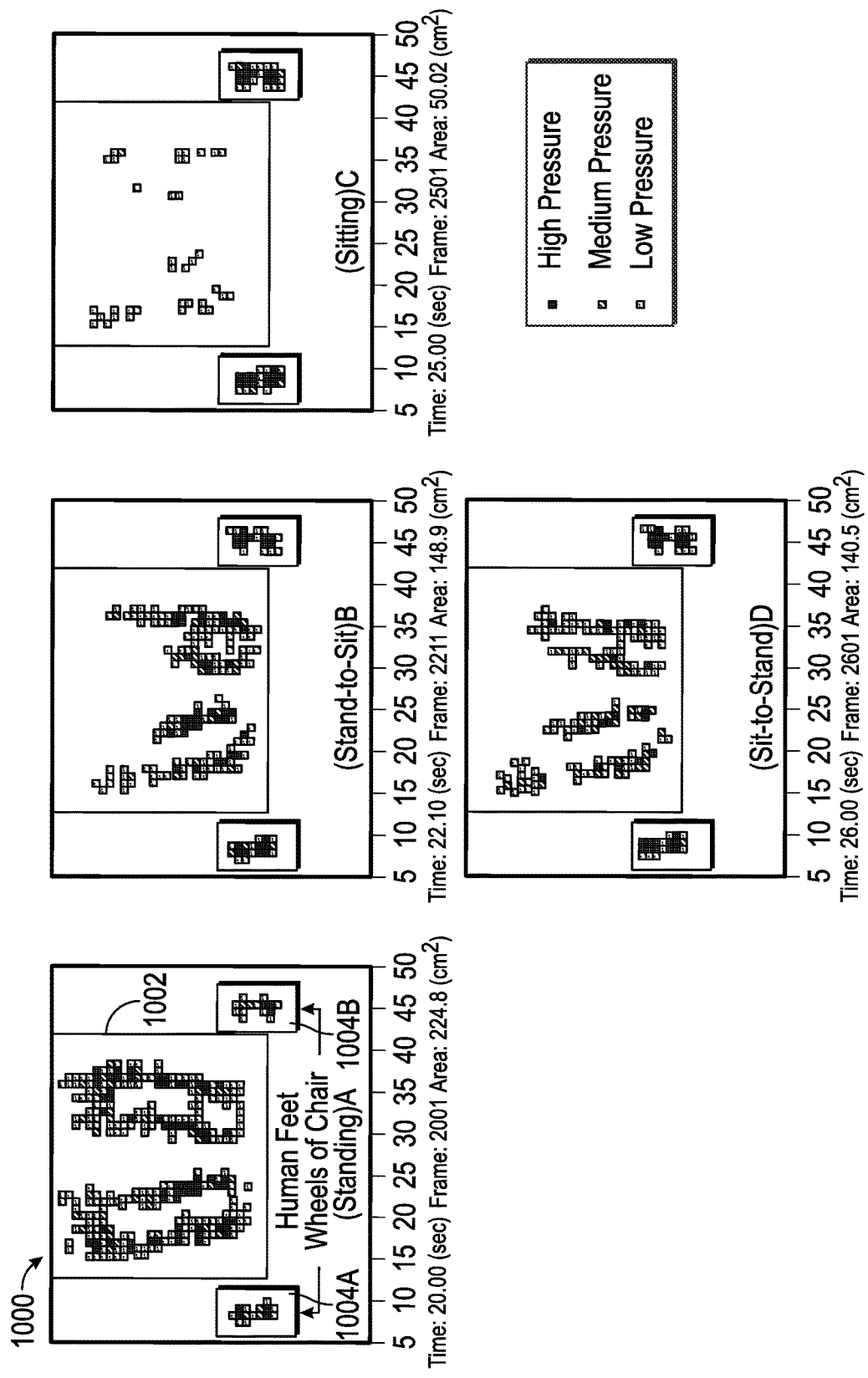
FIGS. 10A-10B show exemplary signal characteristics captured from the carpet of FIG. 1 by the system of FIG. 2, in an embodiment.
Figure 10B:
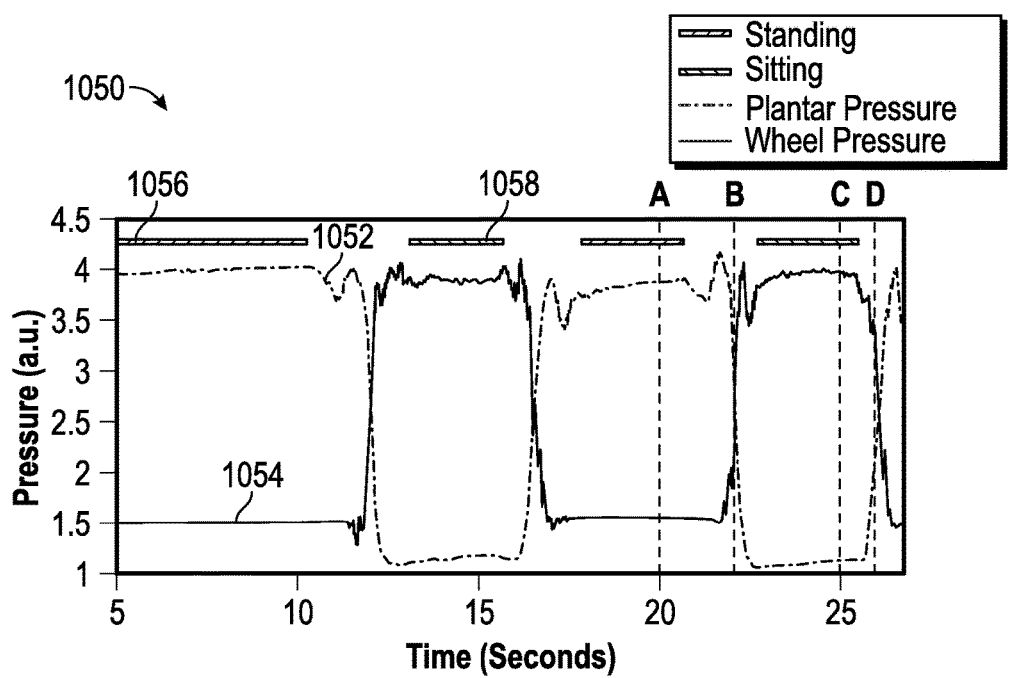

FIG. 10 shows exemplary signal characteristics captured from carpet 100 of FIG. 1 by system 200 of FIG. 2. More specifically, FIG. 10A shows a map 1000 detailing the location of the clusters of the carpet 100 on which pressure is being applied (using, e.g., the tracking scenario 306 of FIG. 3), and the relative pressure being applied to constituents (e.g., square blocks) of these clusters. FIG. 10B shows a graphical illustration 1050 that corresponds to the map 1000.

The map 1000 and the corresponding graphic illustration 1050, as shown in FIGS. 10A-10B, detail how various characteristics of a monitored individual may be determined in an example embodiment. In the FIGS. 10A-10B example, the characteristics shown in map 1000 and graph 1050 include: A) standing movements, B) stand-to-sit movement, C) sitting movement; and D) sit-to-stand movement.

In an embodiment, the map 1000 may be displayed on the display (e.g., display 246 of monitoring computer 204) as a color-coded map that shows the relative pressure being applied to different areas of the carpet 100. For example, the square blocks of the carpet 100 may be represented as red blocks, green blocks, blue blocks, yellow blocks, et cetera, to illustrate the carpet areas on which successively lower pressure is being applied. In this way, the map 1000 may denote not only the pertinent areas of the larger carpet 100 on which pressure is being applied, but also the relative pressure being applied to the sensors in these areas. In the FIG. 10 example, the map 1000 includes boxes 1002 and 1004A, 1004B. The box 1002 represents the plantar pressure being applied to the carpet 100 by the monitored individual, whereas boxes 1004A and 1004B respectively show left and right wheels of a chair (e.g., a wheelchair).

The graphical illustration 1050 shows the plantar pressure signal graphed against time. More specifically, the graph 1050 has pressure (e.g., in atmospheric units or another unit) on the y-axis and time (e.g., in seconds) on the x-axis. The signal 1052 shows the pressure being applied to the carpet 100 at various times by the feet of the monitored individual, which are also shown in map 1000. The signal 1054 shows the pressure being applied to the carpet 100 at various times by the wheels of the wheelchair (or another chair), as also shown in map 1000. The graph 1050 also demarcates standing condition 1056 and sitting condition 1058, respectively.

Turning now to the map 1000, standing A may be identified where the area on the carpet 100 on which pressure is applied is in the shape of feet (see box 1002), and the applied pressure is relatively high. Map 1000 likewise shows that the pressure being applied by the wheelchair wheels (as indicated in boxes 1004A, 1004B) is low in comparison, which would be expected when the monitored individual is in a standing condition A.

Graph 1050 illustrates these concepts further. As can be seen, when the monitored individual is standing (i.e., at the time corresponding to "A" in graph 1050), the pressure exerted by the wheels of the wheelchair is low, whereas the plantar pressure is high in comparison.

Stand-to-sit activity B may be identified by the system 200 where the plantar pressure representation (i.e., box 1002) shows that the pressure being applied is less than the pressure applied at standing activity A. As the person is sitting down on the wheelchair (or another chair), the pressure being applied by the wheels (or legs) of the chair is higher as compared to standing activity A. This is also illustrated in graph 1050. When the monitored individual is sitting down from a standing position (i.e., at the time corresponding to "B" in graph 1050), the pressure of the wheels is increasing rapidly and the pressure being applied by the feet is quickly decreasing.

Sitting C may be identified where the map 1000 indicates that the pressure being applied by the wheelchair wheels (i.e., boxes 1004A, 1004B) is significant compared to the plantar pressure (shown in box 1002). The artisan will understand that where the monitored individual is sitting, majority of his weight will be borne by the wheelchair as opposed to the feet of the monitored individual. Graph 1050 likewise indicates that when sitting C (i.e., at the time corresponding to "C" in graph 1050), the pressure being applied by the wheelchair wheels (or other chair's legs) is significant whereas the pressure being applied by the feet of the monitored individual is negligible.

Sit-to Stand activity D may be identified by the system 200 where the map 1000 indicates that the plantar pressure being applied (and as seen in box 1002) is comparable to the pressure being applied to the carpet 100 by the wheels of wheelchairs (as seen in boxes 1004A, 1004B). Graph 1050 illustrates that when the individual is standing up from a sitting position (i.e., at the time corresponding to "D" in the graph 1050), the pressure being applied by the wheelchairs wheel is decreasing whereas the plantar pressure increases correspondingly, which may allow the system 200 to determine the standing condition D.

FIG. 11 shows exemplary signal processing by system 200 of FIG. 2 to determine breathing rate and heart rate from data of smart carpet 100 of FIG. 1. First, the system 200 (e.g., monitoring computer 204) may collect the raw data 1102 from the smart carpet 100. The raw data 1102 may then be filtered, as shown in FIG. 11 for example, to yield filtered data 1104 for breathing. The filtered breathing data 1104 may next be compared by the system 200 to reference breathing data 1106 (e.g., expected breathing data), and the comparison may be used to estimate the breathing rate of the monitored individual. As noted above, different reference breathing data 1106 may be chosen when estimating the breathing rate of different monitored individuals, or when estimating the breathing rate of individuals during certain activities (e.g., walking, running, et cetera). If the evaluation shows the existence of an abnormal condition (e.g., if the filtered breathing data 1104 does not correspond generally to the expected breathing data 1106 for a time period), an alarm (e.g., alarm actuator 242) may be actuated to apprise monitoring personnel of the emergency event.

In an example embodiment, the heart rate may be similarly evaluated. Specifically, the raw carpet data 1102 may be filtered to yield filtered data for heart rate 1108. As shown, different cutoff frequencies may be used to filter the raw data for the breathing and heart rate estimation. The filtered data for heart rate 1108 may then be compared by the system 200 to reference electrocardiogram data 1110 (e.g., expected electrocardiogram data for the monitored individual), and the comparison may be used to estimate the heart rate of the monitored individual. The reference electrocardiogram data 1110 may be chosen to correspond to the expected heart rate of the particular individual being monitored, and may take into account whether the monitored individual is engaged in an activity (e.g., is running).

In this way, thus, the system 200, via the smart carpet 100, may monitor the healthcare of individuals continuously and non-obtrusively, and may apprise remote monitoring personnel in real-time of emergency conditions.

Changes may be made in the above methods and systems without departing from the scope hereof. It should be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. In particular, the following embodiments are specifically contemplated, as well as any combinations of such embodiments that are compatible with one another:

(A) A method of using a smart carpet having a plurality of pressure sensors arranged as a two-dimensional array, each pressure sensor including a block of anti-static foam situated between at least two perpendicularly oriented yarns, including operably coupling to the smart carpet a monitoring computer having a processor and non-transitory memory having computer implemented instructions stored thereon; simultaneously scanning a first part of the smart carpet at a first frequency and a second part of the smart carpet at a second frequency greater than the first frequency; receiving carpet data from the smart carpet over a communication pathway; and processing the carpet data using the computer implemented instructions to determine each of a physiological activity and a physical activity.

(B) The method of using the smart carpet to monitor the health status of the individual denoted above as (A), including the step of generating an alarm upon determining an emergency condition.

(C) Either of the methods of using the smart carpet to monitor the health status of the individual denoted above as (A) and (B), wherein the alarm is communicated to remote monitoring personnel in real time.

(D) Any of the methods of using the smart carpet to monitor the health status of the individual denoted above as (A)-(C), further including the step of evaluating the carpet data to estimate a breathing rate of the individual.

(E) Any of the methods of using the smart carpet to monitor the health status of the individual denoted above as (A)-(D), wherein estimation of the breathing rate includes filtering the carpet data to obtain filtered breathing data and comparing the filtered breathing data to a reference signal.

(F) Any of the methods of using the smart carpet to monitor the health status of the individual denoted above as (A)-(E), wherein the evaluation comprises using the carpet data to estimate a heart rate of the individual.

(G) Any of the methods of using the smart carpet to monitor the health status of the individual denoted above as (A)-(F), including filtering the carpet data to obtain filtered heart rate data and comparing the filtered heart rate data to a reference heart rate signal, the reference heart rate signal being disparate from the reference breathing signal.

(H) Any of the methods of using the smart carpet to monitor the health status of the individual denoted above as (A)-(G), including the step of determining a balance problem in the individual.

(I) Any of the methods of using the smart carpet to monitor the health status of the individual denoted above as (A)-(H), wherein the balance problem is determined when the carpet data indicates at least one of an asymmetrical standing balance, an abnormal walking speed, and an irregular walking pattern.

(J) Any of the methods of using the smart carpet to monitor the health status of the individual denoted above as (A)-(I), further comprising processing the carpet data to categorize the physical activity as one of a static activity and a dynamic activity.

(K) Any of the methods of using the smart carpet to monitor the health status of the individual denoted above as (A)-(J), wherein based on the processing, the static activity is categorized as one of a sitting activity, a standing activity, a lying activity, a sit-to-stand activity, and a stand-to-sit activity.

(L) Any of the methods of using the smart carpet to monitor the health status of the individual denoted above as (A)-(K), further comprising determining the sit-to-stand activity where at least one of: (a) plantar pressure on the second part increases rapidly; and (b) pressure applied to the second part by an object decreases rapidly.

(M) Any of the methods of using the smart carpet to monitor the health status of the individual denoted above as (A)-(L), wherein the object applying the pressure to the second part is a chair.

(N) Any of the methods of using the smart carpet to monitor the health status of the individual denoted above as (A)-(M), further comprising determining the sit-to-stand activity by comparing plantar pressure on the second part with pressure applied by a chair.

(O) Any of the methods of using the smart carpet to monitor the health status of the individual denoted above as (A)-(N), further comprising displaying a map illustrating relative pressure being applied to each pressure sensor constituting the second part.

(P) Any of the methods of using the smart carpet to monitor the health status of the individual denoted above as (A)-(O), wherein each of the first part and the second part are adaptively selected based on the physical activity.

(Q) Any of the methods of using the smart carpet to monitor the health status of the individual denoted above as (A)-(P), further comprising the step of estimating a body weight of the individual during the standing activity.

(R) Any of the methods of using the smart carpet to monitor the health status of the individual denoted above as (A)-(Q), wherein each of the heart rate and the breathing rate is estimated during each of the sitting activity and the lying activity.

(S) Any of the methods of using the smart carpet to monitor the health status of the individual denoted above as (A)-(R), wherein the categorized dynamic activity includes at least one of walking, running, and falling.

(T) Any of the methods of using the smart carpet to monitor the health status of the individual denoted above as (A)-(S), wherein the alarm is generated upon a determination that the individual has fallen and is unable to rise from the smart carpet for a time period.

(U) Any of the methods of using the smart carpet to monitor the health status of the individual denoted above as (A)-(T), further comprising processing the carpet data to measure the timing and distance of two consecutive steps to determine temporal and spatial parameters of gait.

(V) Any of the methods of using the smart carpet to monitor the health status of the individual denoted above as (A)-(U), further comprising processing the carpet data to detect an urgent event selected from the group including (a) a slow or stopped heart rate during an identified sitting event or an identified fall event, (b) a slow or stopped respiration rate during the identified sitting event or the identified fall event, and (c) an inability of the person to rise from the carpet after the identified fall event; and sending an alert in response to the detected urgent event.

(W) Any of the methods of using the smart carpet to monitor the health status of the individual denoted above as (A)-(V), further comprising processing the carpet data to identify a frailty status based upon at least one of (i) a non-linear postural transition duration, (ii) a number of steps required to complete a turn, (iii) a number of flopping and cautious sitting occurrences during a predefined period, (iv) a difference between heart rate during static sitting and static standing, (v) spatial and temporal parameters of gait, (vi) a number of steps required to complete gait initiation, (vii) a duration of static standing and static sitting, and (viii) gait variability.

(X) Any of the methods of using the smart carpet to monitor the health status of the individual denoted above as (A)-(W), further comprising situating the smart carpet on stairs to determine an up-the-stairs activity.

(Y) A smart carpet system for monitoring a health status of an individual, comprising a smart carpet having electronics and a plurality of pressure sensing areas for sensing plantar pressure of the individual; and a monitoring computer comprising a processor, and a memory communicatively coupled to the processor and storing machine readable instructions; the instructions, when executed by the processor, capable of scanning a first part of the smart carpet at a first frequency and a second part of the smart carpet at a second frequency greater than the first frequency, receiving plantar pressures from the second part, evaluating the plantar pressures to determine at least one of a physical activity and a physiological activity, and communicating to monitoring personnel an alarm upon determining an emergency condition.

(Z) The smart carpet system for monitoring a health status of an individual denoted at (Y), wherein the electronics include each of a multiplexer, a demultiplexer, and an analog to digital converter.

(AA) Either of the smart carpet systems for monitoring a health status of an individual denoted at (Y)-(Z), wherein the monitoring computer is coupled to the smart carpet via a communication pathway that extends from the analog to digital converter.

(BB) Any of the smart carpet systems for monitoring a health status of an individual denoted at (Y)-(AA), further comprising a remote server to receive and store results of the evaluation.

(CC) A smart carpet system for monitoring a health status of an individual, comprising a smart carpet having electronics and a plurality of pressure sensing areas for sensing plantar pressure of the individual; an activity-determining processor configured to implement machine readable instructions to determine at least one of a physical activity and a physiological activity; an interface configured to communicate results of the determination to remote monitoring personnel; and an alarm generator configured to generate an alarm when the results indicate an emergency event.

What is claimed is:

1. A method of using a smart carpet to monitor a health status of an individual, the smart carpet comprising a plurality of pressure sensors arranged as a two-dimensional array, each pressure sensor including a block of foam situated between at least two perpendicularly oriented yarns, the foam having resistance that decreases with increasing pressure, the method comprising:
    operably coupling, to the smart carpet, a monitoring computer having a processor and memory with computer implemented instructions stored thereon;
    simultaneously scanning a first part of the smart carpet at a first frequency and a second part of the smart carpet at a second frequency greater than the first frequency;
    receiving carpet data from the smart carpet over a communication pathway;
    processing the carpet data using the computer implemented instructions to determine each of a physiological activity and a physical activity; and
    generating an alarm upon determining an emergency condition from the carpet data, the alarm specifying the emergency condition, wherein the alarm is communicated to remote monitoring personnel in real time, and wherein the emergency condition is determined by a detected balance problem, wherein the balance problem is determined when the carpet data indicates at least one of an asymmetrical standing balance, an abnormal walking speed, and an irregular walking pattern;
    processing the carpet data to categorize the physical activity as one of a static activity and a dynamic activity, wherein the categorized dynamic activity includes at least one of walking, running, and falling, and wherein the categorized dynamic activity is falling, and the alarm is generated upon a determination that the individual has fallen and is unable to rise from the smart carpet for a time period;
    processing the carpet data to measure the timing and distance of two consecutive steps to determine temporal and spatial parameters of gait;
    processing the carpet data to detect an urgent event selected from the group including (a) a slow or stopped heart rate during an identified sitting event or an identified fall event, (b) a slow or stopped respiration rate during the identified sitting event or the identified fall event, and (c) an inability of the person to rise from the carpet after the identified fall event; and
    sending an alert in response to the detected urgent event.

2. The method of claim 1 further comprising processing the carpet data to identify a frailty status based upon at least one of (i) a non-linear postural transition duration, (ii) a number of steps required to complete a turn, (iii) a number of flopping and cautious sitting occurrences during a predefined period, (iv) a difference between heart rate during static sitting and static standing, (v) spatial and temporal parameters of gait, (vi) a number of steps required to complete gait initiation, (vii) a duration of static standing and static sitting, and (viii) gait variability.

3. The method of claim 2 further comprising situating the smart carpet on stairs to determine an up-the-stairs activity.

* * * * *